United States Patent
Beuermann et al.

(10) Patent No.: US 7,351,587 B2
(45) Date of Patent: Apr. 1, 2008

(54) METHOD FOR THE ONLINE DETERMINATION OF HYDROGEN PEROXIDE

(75) Inventors: Thomas Beuermann, Mannheim (DE); Joaquim Henrique Teles, Otterstadt (DE)

(73) Assignee: BASF Aktiengesellschaft, Ludwigshafen (DE)

(*) Notice: Subject to any disclaimer, the term of this patent is extended or adjusted under 35 U.S.C. 154(b) by 204 days.

(21) Appl. No.: 10/467,278

(22) PCT Filed: Feb. 5, 2002

(86) PCT No.: PCT/EP02/01178

§ 371 (c)(1), (2), (4) Date: Aug. 6, 2003

(87) PCT Pub. No.: WO02/063285

PCT Pub. Date: Aug. 15, 2002

(65) Prior Publication Data

US 2004/0048329 A1     Mar. 11, 2004

(30) Foreign Application Priority Data

Feb. 7, 2001   (DE) ................. 101 05 528

(51) Int. Cl.
- *G01N 33/00*   (2006.01)
- *G01N 21/01*   (2006.01)
- *G01N 21/00*   (2006.01)
- *C07D 301/12*  (2006.01)

(52) U.S. Cl. .................. 436/135; 250/435; 422/82; 549/531

(58) Field of Classification Search ............... 436/135; 250/435; 422/82; 549/531
See application file for complete search history.

(56) References Cited

U.S. PATENT DOCUMENTS

| | | | | |
|---|---|---|---|---|
| 4,418,203 A | * | 11/1983 | Kim ........................ | 549/531 |
| 4,670,385 A | | 6/1987 | Babb et al. | |
| 5,066,462 A | | 11/1991 | Kawasaki et al. | |
| 5,139,956 A | * | 8/1992 | Schick et al. ............ | 436/52 |
| 5,474,938 A | * | 12/1995 | Jadesjo et al. ........... | 436/135 |
| 5,710,012 A | * | 1/1998 | Nikolyukin et al. ...... | 435/28 |
| 5,859,265 A | * | 1/1999 | Muller et al. ............ | 549/531 |
| 5,879,629 A | * | 3/1999 | Capuano et al. .......... | 422/82 |
| 6,037,484 A | | 3/2000 | Grey | |
| 6,518,441 B2 | * | 2/2003 | Grosch et al. ............ | 549/531 |

FOREIGN PATENT DOCUMENTS

| | | |
|---|---|---|
| DE | 101 21 194 | 10/2002 |
| EP | 0 314 046 | 5/1989 |
| EP | 0 712 852 | 5/1996 |
| JP | 63 291594 | 11/1988 |
| JP | 04 036196 | 2/1992 |
| SU | 1 286 995 | 1/1987 |

* cited by examiner

*Primary Examiner*—Jill Warden
*Assistant Examiner*—Lore Ramillano
(74) *Attorney, Agent, or Firm*—Oblon, Spivak, McClelland, Maier & Neustadt, P.C.

(57) ABSTRACT

A process for the on-line determination of the hydrogen peroxide content of a mixture obtained in a chemical reaction comprises at least the following steps:
(1) admixing the mixture comprising hydrogen peroxide with at least one reagent which is capable of forming a substance which can be detected by optical methods on reaction with hydrogen peroxide, so as to form this substance,
(2) determining the amount of the substance present by measuring its specific absorption in an appropriate wavelength range.

12 Claims, 3 Drawing Sheets

METHOD FOR THE ONLINE DETERMINATION OF HYDROGEN PEROXIDE

Figure 1:
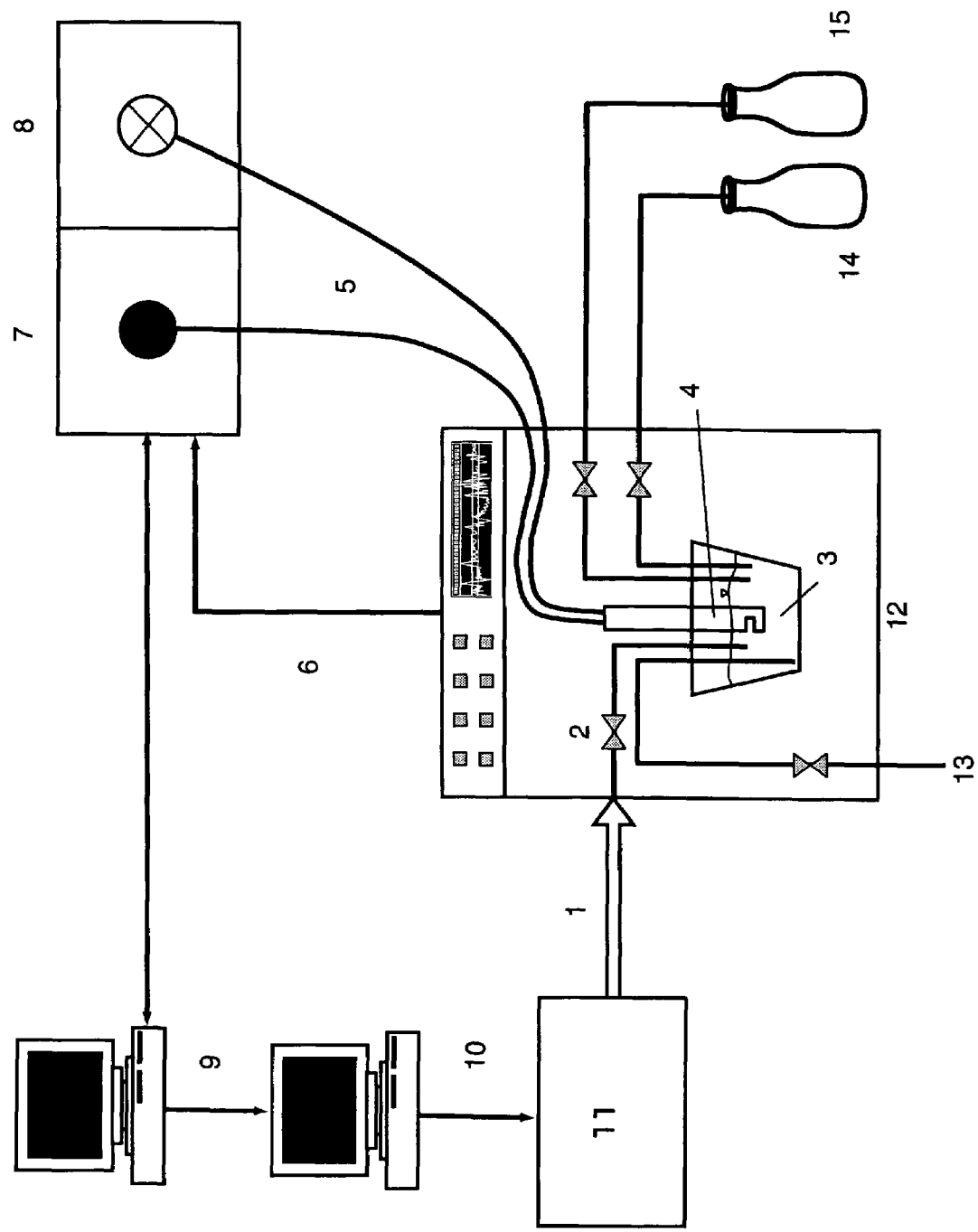

The present invention relates to an on-line method of determining the hydrogen peroxide content of a mixture obtained in a chemical reaction and also to a process for the oxidation of an alkene by means of hydrogen peroxide in the presence of a zeolite catalyst into which this method is integrated.

The conversion of starting materials in chemical synthesis is generally determined from their concentration in the synthesis solution or the product mixture from the synthesis. Particularly in the case of reactions carried out continuously, it is often desirable to keep the conversion of one or more starting materials within narrow limits. To achieve this, it is necessary to take samples from the synthesis mixture at particular time intervals during the synthesis process and to determine the concentration of the respective starting material in these samples. If the residual concentration of the starting material found in the product mixture deviates from the optimum prescribed value, it is possible, for example, to readjust the addition of the starting materials or to modify the reaction conditions (e.g. temperature or pH) to bring the conversion back to the desired value.

A particularly important case is oxidation reactions using hydrogen peroxide.

To determine the concentration of hydrogen peroxide in a mixture obtained in a chemical reaction, many analytical methods are generally available to a person skilled in the art. In principle, hydrogen peroxide can be determined both quantitatively and qualitatively by taking advantage of its oxidizing and reducing properties.

For example, hydrogen peroxide can be detected qualitatively by means of the reaction with a titanium(IV) oxide sulfate solution. An intensive yellow color develops as a result of the formation of a titanium(IV) peroxy complex. Another qualitative method of detection is the reaction with potassium dichromate solution and dilute sulfuric acid, which results in the reaction solution becoming blue.

On the other hand, quantitative determination is carried out, for example, by means of oximetric titration with potassium permanganate, sodium iodide or cerium(IV) sulfate, as is well known to a person skilled in the art.

Difficulties in the analysis of hydrogen peroxide can arise from the presence of organic hydroperoxides, for example hydroperoxypropanols, in the analysis solution, since these also react with $KMnO_4$, NaI and cerium(IV) sulfate.

The determination of hydrogen peroxide is likewise problematical when the amount to be determined is very low, i.e. generally below 1% by weight.

A further problem occurs when the mixture in which the concentration of hydrogen peroxide is to be determined is very complex in nature, i.e. when further substances apart from the substance to be determined are present in the analysis solution. Examples which may be mentioned are further unreacted starting materials and by-products formed in addition to the main product.

Thus, a determination of hydrogen peroxide in synthesis solutions having a low concentration of hydrogen peroxide or/and a complex nature can in general not be carried out directly by means of measurements such as optical absorption, reflection or emission, for example fluorescence or phosphorescence.

Furthermore, measurement of the absorption of hydrogen peroxide in the near infrared region, e.g. FT-NIR spectroscopy in the range from 4631 to 5140 $cm^{-1}$, fails for the above reasons and also due to interference by water and organic hydroperoxides.

Furthermore, measurement of the absorption of hydrogen peroxide in the ultraviolet region, e.g. measurement of the UV absorption at 254 or 280 nm, is suitable for the reliable determination of the concentration of hydrogen peroxide only in water/methanol solutions. If organic hydrogen peroxides are present in the synthesis solution, reliable analysis of hydrogen peroxide by this method is no longer possible.

In contrast, colorimetric methods are well suited to the selective determination of hydrogen peroxide in synthesis solutions having a complex nature and/or a low hydrogen peroxide content. In these methods, the sample to be analyzed is reacted with a suitable reagent to form a substance which absorbs or fluoresces in the UV/VIS region of the spectrum and can thus be determined.

For example, the determination of hydrogen peroxide by the "enzymatic method using peroxidase" is based on the oxidation of a leuco dye (for example leuco-crystal violet) by the hydrogen peroxide to be determined. This reaction is catalyzed by a peroxidase (e.g. horseradish peroxidase type II, EC No. 1.11.1.7 (AS reg. No. 9003-99-0). The dye formed is subsequently determined photometrically, e.g. at 596 nm in the case of leuco-crystal violet. This method is specific for hydrogen peroxide. Only hydroperoxides which liberate hydrogen peroxide extremely easily in solution lead to interferences. This method is described in detail in H. U. Bergmeyer, "*Methoden der enzymatischen Analyse*", 3rd edition, Vol. II, p. 2297ff., Verlag Chemie, Weinheim (1974).

The "titanium sulfate method" is also suitable for the quantitative colorimetric determination of hydrogen peroxide in the presence of organic hydroperoxides. This determination is adversely affected only by hydroperoxides which tend to liberate hydrogen peroxide in an acidic medium (e.g. hemiperacetals). This method is based on the yellow titanyl peroxo complex formed by the reaction of hydrogen peroxide present with a titanium(IV) reagent (for example titanyl sulfate, titanium(IV) chloride or potassium titanyl oxalate). The titanyl peroxo complex has a strong absorption at about 408 nm. Details of the way in which this method can be carried out may be found in the literature, for example in Kakáč, Z. Vejdelek, "*Handbuch der photometrischen Analyse organischer Verbindungen*", Volume 1, p. 92ff., Verlag Chemie, Weinheim (1974) or in G. M. Eisenberg. Ind. Eng. Chem., Anal. Ed. (1943) 15, 327, and the literature references cited therein.

This method is, as also described in the article by C. B. Allsopp in "*Analyst*" (1941) 66, 371, suitable for determining hydrogen peroxide in a very low concentration range down to $10^{-5}$ N.

A third calorimetric method which is likewise suitable for the selective determination of hydrogen peroxide is the "cobalt hydrogen carbonate method". This is based on the reaction of hydrogen peroxide with Co(II) ions to form a colored cobalt peroxo complex. This has a very strong absorption at about 260 nm. A precise description of this method may be found in the literature known to those skilled in the art, for example in Masschelen, W. "*Spectrophotometric Determination of Residual Hydrogen Peroxide*", Water and Sewerage Works, p. 69, August 1977.

The sensitivity of this method is very high, so that, for example, hydrogen peroxide concentrations of about 0.02 ppm can be detected, but certain compounds formed, for example, as by-products of the oxidation of propylene by hydrogen peroxide (e.g. acetone, which has a cutoff at a wavelength of $\lambda_c < 330$ nm) also absorb in this region and thus interfere in the hydrogen peroxide determination. This is a particular problem at very low concentrations of hydrogen peroxide of about <100 ppm of $H_2O_2$.

When carrying out such reactions, for example the oxidation of an alkene by means of hydrogen peroxide in the presence of a zeolite catalyst, an optimum yield should be achieved, but at the same time reliable control of the reaction has to be ensured. To achieve this, it is necessary to monitor the hydrogen peroxide concentration on-line.

In general, an analytical method whose end points can be indicated photometrically can also be carried out by means of automated analytical instruments. Their use in a synthesis process has hitherto frequently been separated from the data processing unit for evaluation or process control and is coupled with this only indirectly, i.e. "off-line", if at all.

The "off-line" analytical methods used hitherto for determining hydrogen peroxide in synthesis processes during operation have the disadvantage that there is a time delay between the determination of the hydrogen peroxide concentration and the necessary adjustment of the synthesis conditions.

Due to this time delay, the synthesis conditions cannot be adapted to the changed hydrogen peroxide content sufficiently quickly. Thus, the synthesis does not proceed optimally for this time until the adjustment is made. During this time, increased formation of by-products, for example, can occur. These in turn reduce the yield of the actual product and make its work-up more difficult.

For the reasons mentioned, it has hitherto been virtually impossible to improve the economic efficiency of synthesis processes, for example the oxidation of alkenes by means of hydrogen peroxide in the presence of a catalyst with respect to the yield and purity of the product, by monitoring the hydrogen peroxide concentration.

Furthermore, especially in the case of starting materials such as hydrogen peroxide which tend to undergo exothermic decomposition reactions, safety considerations make it undesirable to allow their concentration in the synthesis mixture to remain uncontrolled for any length of time. Unreacted hydrogen peroxide which is thus present in the output from the synthesis can lead to unsafe situations such as explosive decomposition reactions, for example in the subsequent work-up of the product.

It would therefore be advantageous, especially in the case of batch or semibatch reactions, to have on-line monitoring of the hydrogen peroxide concentration available so as to be able to avoid accumulation of hydrogen peroxide to unacceptably high concentrations which could represent a safety risk.

In the case of an oxidation in a continuous reactor, it is important to monitor the residual content (and thus also the conversion) of hydrogen peroxide in real time and to keep it within predetermined limits by means of alterations to the reaction conditions (e.g. temperature, pH or amounts of starting material). This, too, could be achieved by means of an appropriate on-line determination.

An on-line determination of the hydrogen peroxide content would be of particularly great importance when the oxidation reaction is carried out continuously in the presence of a catalyst whose catalytic activity is not constant (e.g. because of deactivation of the catalyst). To adhere to a prescribed value for the residual hydrogen peroxide content in this case, it is absolutely necessary for the reaction conditions to be continually adjusted to compensate for the changing catalytic activity.

It is an object of the present invention to provide an on-line method of determining the hydrogen peroxide content and a process for the oxidation of alkenes by means of hydrogen peroxide into which this method is integrated, so as to enable the abovementioned disadvantages to be avoided.

We have found that this object is achieved by an on-line method of determining the hydrogen peroxide content of a mixture obtained in a chemical reaction, which method comprises at least the following steps:
(1) admixing the mixture comprising hydrogen peroxide with at least one reagent which is capable of forming a substance which can be detected by optical methods on reaction with hydrogen peroxide, so as to form this substance,
(2) determining the amount of the substance present by measuring its specific absorption in an appropriate wavelength range, and by a process for the oxidation of alkenes by means of hydrogen peroxide in the presence of a catalyst into which this method is integrated.

For the purposes of the present invention, the term "on-line determination of the hydrogen peroxide content" encompasses all methods and apparatuses which are suitable for the determination of hydrogen peroxide and which are directly connected to at least one data processing unit so that it is possible to make adjustments to a synthesis process in order to regulate it. A preferred apparatus for the "on-line determination of the hydrogen peroxide content" is described in DE 101 21 194.5 which was also filed by the applicant of this invention.

The expression "directly" encompasses all ways known to a person skilled in the art in which an instrument can be connected to at least one data processing unit. This connection can, for example, be via further equipment items known to a person skilled in the art. These are able, for example, to receive, to amplify, to transform or to otherwise modulate the signals produced by the analytical apparatus. Furthermore, they can be connected both with one another and with the analytical apparatus and with the data processing unit or units via commercial cable connections, infrared interfaces or similar means of transmitting signals.

In the method of the present invention, the apparatus for the on-line determination of hydrogen peroxide comprises at least one sampling device for taking a sample from the reaction mixture formed in the course of the synthesis, at least one apparatus for sample preparation and at least one instrument which is capable of determining the specific absorption of the sample in a suitable wavelength range. The apparatus in question comprises at least one component which is connected to the equipment items described and is capable of performing the control function for the individual equipment items so as to coordinate their operation.

For process control of the synthesis plant, the data determined by the apparatus for the on-line determination of hydrogen peroxide are evaluated by means of at least one data processing unit connected to this apparatus and converted into control commands for process control of the synthesis plant. These control commands can then be passed on to the process control system of the plant, which is connected to the at least one data processing unit.

A typical mixture used in the present method comprises at least the products formed in the reaction under consideration here, intermediates, by-products and starting materials, e.g. hydrogen peroxide.

Chemical reactions which produce the mixture in which hydrogen peroxide is to be determined with the aid of the method of the present invention can be all chemical reactions known to those skilled in the art in which hydrogen peroxide is, for example, used as starting material or can be formed as by-product or intermediate.

To be able to determine the hydrogen peroxide content by means of the method of the present invention, the mixture obtained is firstly admixed with at least one reagent which reacts with hydrogen peroxide to form a substance which can be detected by optical methods.

Reagents having this property are in principle all compounds known to those skilled in the art for this purpose. They can be used either individually or in admixture with one another or together with further compounds. Further compounds can, for example, comprise stabilizing or solubilizing additives.

In general, the formation of the substance involves reaction of the reagent with hydrogen peroxide to form a complex or a compound which can be detected by means of optical methods. Here, the concentration of the substance and thus the hydrogen peroxide content can be determined by comparison with a suitable standard.

The reagent or reagents is/are preferably selected from the group consisting of metals of transition groups IV to IX of the Periodic Table of the Elements.

The reagent or reagents is/are more preferably selected from the group consisting of titanium-, cobalt-, chromium-, zirconium-, hafnium-, vanadium-, niobium- and tantalum-containing compounds.

For example, the following reagents can be used for this purpose: titanium(IV) compounds such as titanyl sulfate, cobalt(II) salts, for example cobalt(II) sulfate or cobalt bicarbonate, molybdenum(VI) salts, for example ammonium molybdate, vanadium salts such as vanadyl sulfate, etc.

The reagent used is particularly preferably titanyl sulfate or cobalt(II) sulfate.

In a further preferred embodiment of the present invention, the reagent or reagents comprise(s) a leuco dye and a peroxidase.

For the purposes of the present invention, the term "leuco dye" refers to any dye whose oxidized form has a weaker or stronger or other, e.g. shifted in terms of the absorption wavelength, specific absorption in the optical spectrum compared to its reduced form.

Preference is here given to using leuco-crystal violet (tris(4-dimethylaminophenyl)-methane), leuco-malachite green (bis(4-dimethylaminophenyl)phenylmethane), o-dianisidine and acridinium salts, e.g. 10-methyl-α-(p-formylphenyl)acridinium carboxylates and purpurogallin.

Particular preference is given to using leuco-crystal violet (tris(4-dimethylaminophenyl)-methane) or purpurogallin.

In the reaction of hydrogen peroxide with the respective leuco dye, the formation of a substance which is detectable by optical methods proceeds via an electron transfer reaction which is catalyzed by a peroxidase. The leuco dye is oxidized in this reaction. The oxidized form of the leuco dye then absorbs at a wavelength which is specific to it and can thus be detected by means of optical methods. Here too, the concentration of oxidized leuco dye and thus the concentration of hydrogen peroxide can be determined by comparison with a suitable standard.

A peroxidase suitable for this embodiment of the present invention is, for example, peroxidase type II (from horseradish), which is commercially available.

Basically, the substance formed by reaction of the hydrogen peroxide to be determined with the respective reagent can be detected with the aid of appropriate optical methods on the basis of its specific absorption in a particular wavelength range.

It is in principle possible to use all optical methods known to those skilled in the art for the detection of a substance which absorbs in a particular wavelength range.

Methods which may be mentioned by way of example are UV, UV/VIS, VIS, IR, NIR and Raman spectroscopy. It is possible to determine either the absorption (or transmission), the reflection or the fluorescence.

In a preferred embodiment of the invention, the amount of the substance present is determined by measuring its specific absorption and/or fluorescence in the UV/VIS region of the spectrum.

Instruments suitable for detection of the substance for the purposes of the present invention are generally commercial spectrometers appropriate for the respective wavelength range, preferably spectrometers operating in the UV/VIS region.

The present invention further provides a process for the oxidation of an alkene, which comprises reacting the alkene with hydrogen peroxide in the presence of a catalyst, preferably a zeolite catalyst. In this process, the hydrogen peroxide content of the reaction mixture is determined on-line by means of the above-described method during the reaction.

For the purposes of the present invention, the term "alkene" refers to all compounds which have at least one C-C double bond.

Examples of such organic compounds having at least one C-C double bond are the following alkenes:

ethene, propene, 1-butene, 2-butene, isobutene, butadiene, pentenes, piperylene, hexenes, hexadienes, heptenes, octenes, diisobutene, trimethylpentene, nonenes, dodecene, tridecene, tetradecene to eicosene, tripropene and tetrapropene, polybutadienes, polyisobutenes, isoprenes, terpenes, geraniol, linalool, linalyl acetate, methylenecyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, diphenylbutadiene, Vitamin A, beta-carotene, vinylidene fluoride, allyl halides, crotyl chloride, methallyl chloride, dichlorobutene, allyl alcohol, methallyl alcohol, butenols, butenediols, cyclopentenediols, pentenols, octadienols, tridecenols, unsaturated steroids, ethoxyethene, isoeugenols, anethole, unsaturated carboxylic acids such as acrylic acid, methacrylic acid, crotonic acid, maleic acid, vinylacetic acid, unsaturated fatty acids such as oleic acid, linoleic acid, palmitic acid, naturally occurring fats and oils.

In the process of the invention, preference is given to using alkenes containing from 2 to 18 carbon atoms. Particular preference is given to reacting ethene, propene and butene. Very particular preference is given to reacting propene.

The hydrogen peroxide used for the reaction with an alkene in the process of the present invention can be prepared, for example, with the aid of the anthraquinone process by means of which virtually the entire amount of the hydrogen peroxide produced worldwide is obtained. This process is based on the catalytic hydrogenation of an anthraquinone compound to form the corresponding anthrahydroquinone compound, subsequent reaction of this with oxygen to form hydrogen peroxide and subsequent extraction to separate off the hydrogen peroxide formed. The catalysis cycle is closed by a new hydrogenation of the anthraquinone compound which has been formed again in the reaction with oxygen.

An overview of the anthraquinone process is given in "Ullmanns Encyclopedia of Industrial Chemistry", 5th edition, volume 13, pages 447 to 456.

It is likewise conceivable to obtain hydrogen peroxide by conversion of sulfuric acid into peroxodisulfuric acid by anodic oxidation with simultaneous evolution of hydrogen at the cathode. Hydrolysis of the peroxodisulfuric acid then leads via peroxosulfuric acid to hydrogen peroxide and sulfuric acid, which is thus recovered.

Of course, preparation of hydrogen peroxide from the elements is also possible.

Before use of hydrogen peroxide in the process of the present invention, it is possible, for example, for a commercially available hydrogen peroxide solution to be freed of undesirable ions. Conceivable methods are, inter alia, methods as are described, for example, in WO 98/54086, DE-A 42 22 109 or WO 92/06918. Likewise, at least one salt which is present in the hydrogen peroxide solution can be removed from the hydrogen peroxide solution by means of ion exchange in an apparatus comprising at least one nonacidic ion exchange bed having a cross-section of stream area A and a height H such that the height H of the ion exchange bed is less than or equal to $2.5 \times A^{1/2}$, in particular less than or equal to $1.5 \times A^{1/2}$. For the purposes of the present invention, it is in principle possible to use all nonacidic ion exchange beds comprising cation exchangers or anion exchangers. It is also possible to use mixed beds of cation and anion exchangers as ion exchange beds. In a preferred embodiment of the present invention, only one type of nonacidic ion exchangers is used. Further preference is given to the use of a basic ion exchanger, particularly preferably a basic anion exchanger and very particularly preferably a weak base anion exchanger.

As regards the zeolite catalysts which can be used for the purposes of the present invention, there are no particular restrictions.

Zeolites are, as is known, crystalline aluminosilicates having ordered channel and cage structures containing micropores which are preferably smaller than about 0.9 nm. The network of such zeolites is made up of $SiO_4$ and $AlO_4$ tetrahedra which are joined via shared oxygen bridges. An overview of known structures is given, for example, in W. M. Meier, D. H. Olson and Ch. Baerlocher, "Atlas of Zeolite Structure Types", Elsevier, 4th edition, London 1996.

Zeolites which contain no aluminum and in which the Si(IV) in the silicate lattice is partly replaced by titanium as Ti(IV) are also known. These titanium zeolites, in particular those having a crystal structure of the MFI type, and possible ways of preparing them are described, for example, in EP-A0 311 983 or EP-A 405 978. Apart from silicon and titanium, such materials may further comprise additional elements such as aluminum, zirconium, tin, iron, cobalt, nickel, gallium, boron or small amounts of fluorine. In the zeolite catalysts which are preferably regenerated using the process of the present invention, the titanium of the zeolite can be partly or completely replaced by vanadium, zirconium, chromium or niobium or a mixture of two or more thereof. The molar ratio of titanium and/or vanadium, zirconium, chromium or niobium to the sum of silicon and titanium and/or vanadium and/or zirconium and/or chromium and/or niobium is generally in the range from 0.01:1 to 0.1:1.

Titanium zeolites, especially those having a crystal structure of the MFI type, and possible ways of preparing them are described, for example, in WO 98/55228, WO 98/03394, WO 98/03395, EP-A 0 311 983 or EP-A 0 405 978, whose relevant disclosure is fully incorporated by reference into the present patent application.

Titanium zeolites having an MFI structure can, as is known, be identified by means of a particular X-ray diffraction pattern and also by means of a lattice vibration band in the infrared region (IR) at about 960 $cm^{-1}$ and can thus be distinguished from alkali metal titanates or crystalline and amorphous $TiO_2$ phases.

Specific examples of suitable zeolites are titanium-, germanium-, tellurium-, vanadium-, chromium-, niobium- and zirconium-containing zeolites having a pentasil zeolite structure, in particular the types which can be assigned X-ray-crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structures and to mixed structures made up of two or more of the abovementioned structures. It is also possible for titanium-containing zeolites having the ITQ-4, SSZ-24, TIM-1, UTD-1, CIT-1 or CIT-5 structure to be used in the process of the present invention. Further titanium-containing zeolites which may be mentioned are those having the ZSM-48 or ZSM-12 structures.

For the purposes of the present invention, preference is given to using Ti-zeolites having an MFI, MEL or mixed MFI/MEL structure. Preference is also given specifically to the Ti-containing zeolite catalysts generally referred to as "TS-1", "TS-2", "TS-3", and also Ti zeolites having a framework structure which is isomorphous with β-zeolite.

Accordingly, the present invention also provides a process as described above in which the catalyst is a titanium silicalite having the TS-1 structure.

When carrying out the process, it has surprisingly been found that the on-line determination of the hydrogen peroxide content enables the running synthesis process to be optimally controlled. The determination is, in particular, carried out on the product mixture from the reaction. In a synthesis carried out in a number of reactors connected in series, the determination is preferably carried out on the product mixture from either individual, selected reactors or from all reactors. In this way, the total yield or the yield from each reactor and the purity of the respective reaction mixture and thus also of the product can be optimized. Furthermore, the safety risk resulting from any hydrogen peroxide present in the product mixture from a synthesis without optimized control can be minimized.

For the purposes of the present invention, the determination of the hydrogen peroxide content during the course of the process of the present invention is carried out mainly periodically, preferably at a frequency in the range from 0.5 to 100 $h^{-1}$. Particular preference is given to frequencies in the range from 1 to 60 $h^{-1}$.

For example, on the basis of the relationship between the following factors:
 the temperature prevailing in the reactor,
 the conversion of hydrogen peroxide and
 the catalytic activity of the catalyst used in the reaction, deactivation of the catalyst used in each case can be countered by continuously increasing the temperature or adjusting the pH, as described in DE 199 36 547.4.

The temperature increase required for each regulated step is determined with the aid of the determination of the hydrogen peroxide content of the respective reactor output carried out at short time intervals. As a result of the on-line connection between the apparatus for determining the concentration of hydrogen peroxide and the process control system of the synthesis plant, the necessary regulation occurs without any significant time delay.

As a consequence, the conversion of hydrogen peroxide can be kept constant over virtually the entire synthesis process. This in turn has a positive effect on the yield and purity of the desired product.

In the case of a plurality of reactors connected in series, it is of course also possible, in the context of the invention, to determine the hydrogen peroxide content in each reactor or in the output from each reactor by means of the appropriate number of apparatuses for the on-line determination of the hydrogen peroxide content. One or more data processing units connected to these apparatuses transmit(s) control commands corresponding to the hydrogen peroxide content determined in each case to the process control for the respective reactor. The process control system can thus make regulating adjustments when required.

Accordingly, the present invention also provides a process for the oxidation of an alkene of the type according to the invention in which the reaction is carried out in a plurality of reactors. In this process, the concentration of hydrogen peroxide in at least one reactor, preferably all reactors, can be determined by means of the novel on-line method of determining the hydrogen peroxide content.

The process of the present invention, as described above, is preferably used for the conversion of propene into propylene oxide by means of hydrogen peroxide in methanolic solution in the presence of a titanium silicalite having an MFI structure.

In a particularly preferred embodiment of this reaction to form propylene oxide, propylene is reacted with hydrogen peroxide in the presence of methanol, a basic salt and TS-1 as catalyst in a first reactor (main reactor, for example tubular reactor).

Here, the reaction pressure is selected and kept constant at a value at which no gas phase is present during the reaction. The temperature is selected so that the hydrogen peroxide conversion in the output from the reactor is from 85 to 95%, preferably from 88 to 93%.

Since the catalyst is typically deactivated during the course of the reaction, the temperature has to be continuously adjusted for the abovementioned reasons. In general, the temperature increase necessary is from 0.2 to 1.5° C. per day, depending on the reaction conditions.

To determine the precise temperature increase necessary at a given point in time during the synthesis, the hydrogen peroxide conversion is determined at short time intervals, as described above.

For example, the output from the first reactor is worked up in a distillation column in which at least 90%, typically >99%, of the propylene oxide formed are separated off at the top.

The remaining bottoms are admixed with propylene and, if appropriate, with a basic salt and reacted in a second reactor (after-reactor, for example a simple tube reactor or shaft reactor). In the after-reactor, preferably from 90 to 95% of the hydrogen peroxide introduced into it are reacted, since lower conversions frequently leave residual hydrogen peroxide which can cause safety problems, while higher conversions frequently result in a decrease in the selectivity of the reaction.

To control the conversion in the after-reactor, adjustments are made, for example, to the inlet temperature or the amount of base via the process control system in accordance with the hydrogen peroxide content determined on-line.

The invention is illustrated by the examples below.

EXAMPLE 1

Apparatus for the On-Line Determination of Hydrogen Peroxide

The overall apparatus for the on-line UV/VIS-spectroscopic determination of $H_2O_2$ comprises:
1. a metering and control system (e.g. process titrator from the "ADI" series from Metrohm) for automatic sampling and carrying out the color reaction,
2. a fiber optic transmission probe which dips into the reaction vessel and is connected via silica optic fibers to
3. a UV/VIS spectrometer (preferably a diode array spectrometer) for recording the spectra, and also
4. a computer (PC) for evaluating the spectra and calculating the $H_2O_2$ concentration.
5. The $H_2O_2$ concentrations in the product stream which have been determined in this way can subsequently be converted by means of a digital/analog converter into a 4-20 mA electric signal which is transmitted to a process control system for controlling the plant.

The schematic structure is shown in FIG. 1.

The UV/VIS spectrometer is preferably triggered by the process titrator. In this case, a transmission probe dips into each of the reaction vessels in the process titrators. If these transmission probes are connected via optic fibers (preferably made of quartz) to an optical multichannel multiplexer, one spectrometer is generally sufficient for (virtually) simultaneously recording the absorption spectra at the various measurement points.

Procedure for the $H_2O_2$ Determination:

A few milliliters of sample (typically 0.5-5 ml, depending on the concentration) are taken from the product stream via a capillary line with the aid of the metering system and are transferred into the reaction vessel located in the titrator. The color reagent (commercially available titanyl sulfate solution, about 5% by weight of Ti) (typically 0.5-5 ml) is added from a reservoir. A yellowish titanyl peroxo complex is formed after a short time (typically 1 min). The solution is subsequently made up to a specific volume (typically in the range from 25 to 500 ml) with a solvent (e.g. distilled water, dilute sulfuric acid, etc.).

Figure 2:
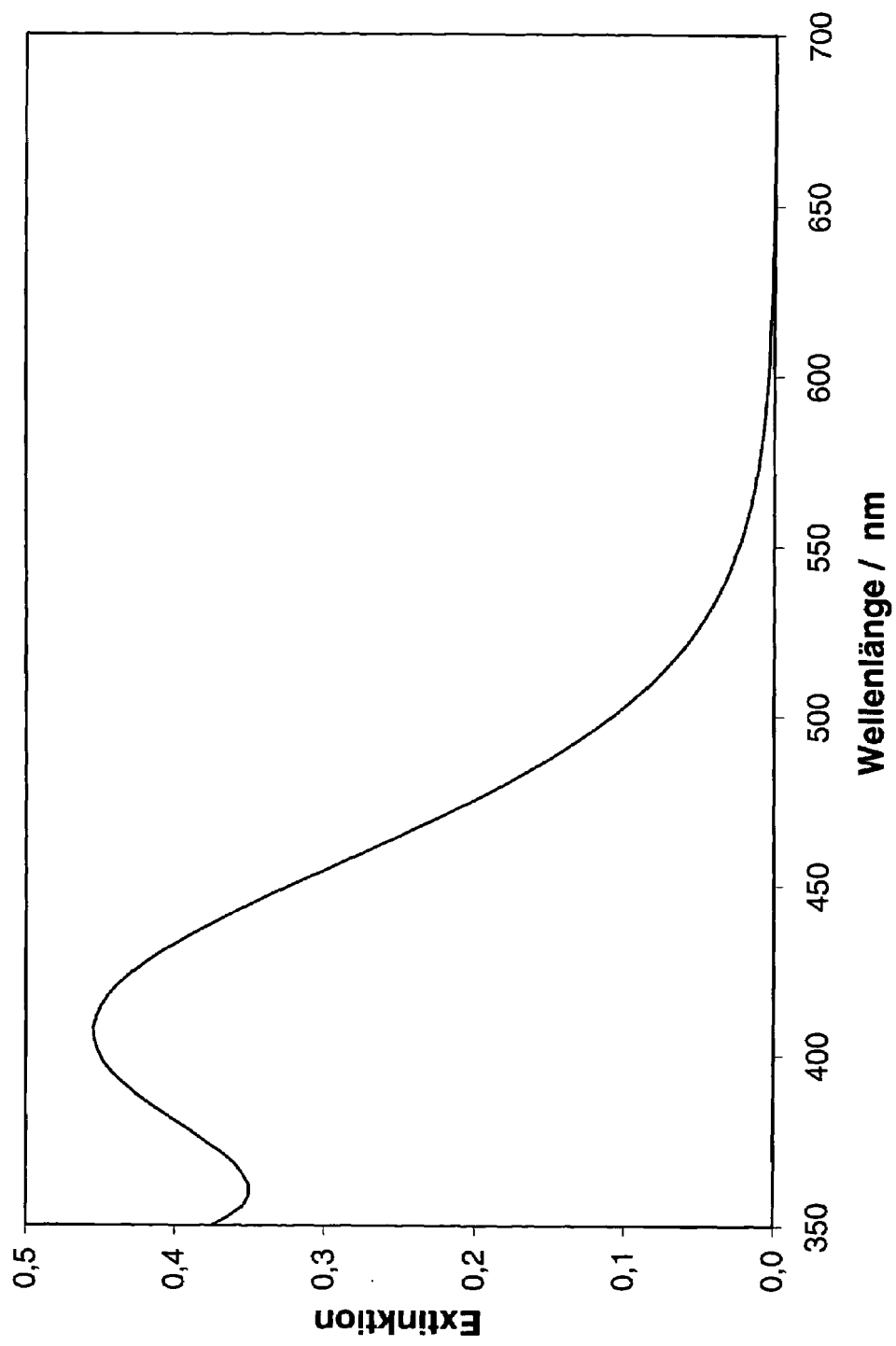

To record the UV/VIS absorption spectrum, it is necessary for the measuring slit of the transmission probe to dip completely into the solution to be analyzed. A typical UV spectrum is shown in FIG. 2. A spectrum previously recorded on the solvent serves as reference (=100% transmission).

The conversion of the measured UV/VIS absorbances into $H_2O_2$ concentrations is carried out on the computer by means of a measurement and evaluation program with the aid of a calibration function. The calculation is preferably carried out using the absorbance at the absorption maximum of the titanyl peroxo complex at about 408 nm.

EXAMPLE 2

Sequence of Steps for the Photometric On-Line Determination of $H_2O_2$

For the on-line determination of hydrogen peroxide in the output from a reactor for the epoxidation of propylene, an apparatus as described in example 1, FIG. 1 was constructed. This comprised the following components:
metering system (ADI 2015 from Metrohm) with control unit and measurement cell,
UV/VIS diode array spectrometer (MCS521 from Zeiss),
computer (spectrometer control, evaluation, data transfer to PCS),
optical immersion probe (from Hellma).

The actual measurement was carried out according to the sequence described below:
1. emptying of the measurement cell (reaction vessel),
2. filling of the measurement cell with solvent (e.g. water) ("blank"),
3. trigger signal to UV/VIS process spectrometer for recording the
4. reference spectrum by means of the transmission probe,
5. measurement cell emptied by means of suction,
6. sample (typically 0.5-5 ml, depending on $H_2O_2$ concentration) transferred (sample drawn by suction via a capillary line from the sampling point and metered into the measurement cell),
7. reagent, viz. titanyl sulfate solution containing about 5% by weight of Ti (typically 0.5-5 ml), depending on $H_2O_2$ concentration, is metered into the measurement cell,
8. pause (a few seconds at room temperature) to allow formation of the titanyl peroxo complex,
9. solution made up to a specific volume (typically 25-500 ml) with solvent (e.g. water),
10. pause,
11. trigger signal to spectrometer for recording the UV/VIS absorption spectrum of the reaction solution,
12. evaluation program on the computer calculates the $H_2O_2$ concentration from the absorbance,
13. transmission of the $H_2O_2$ concentration from the computer to the process control system of the synthesis plant,
14. emptying of the measurement cell,
15. rinsing of the measurement cell with solvent.

After a defined delay time, the sequence starts afresh at item 1.

EXAMPLE 3

The epoxidation of propylene by means of hydrogen peroxide was carried out in a tube reactor which had a diameter of 45 mm and a length of 2 m, was provided with a cooling jacket and was charged with about 620 g of a fresh epoxidation catalyst (titanium silicalite TS-1 in the form of extrudates having a diameter of 1.5 mm). The amounts of the individual starting materials used were as follows:

| | |
|---|---|
| Methanol: | 1834 g/h |
| Hydrogen peroxide (40% in water): | 332 g/h |
| Propene: | 244 g/h |
| $K_2HPO_4$ solution (1.25% by weight in water): | 4 g/h |

The individual starting materials were combined under superatmospheric pressure (about 20 bar) upstream of the reactor and then passed through the reactor. The temperature of the cooling medium in the jacket was about 30° C. at the beginning of the experiment. When the conversion began to decrease, the temperature of the cooling medium was adjusted so that a constant conversion of hydrogen peroxide was achieved. The conversion was determined by on-line determination of the hydrogen peroxide in the output from the reactor, as described in examples 1 and 2.

An additional sample was taken once per day and analyzed off-line by the titanyl sulfate method to provide a comparison. The comparison of the results of the on-line and off-line determinations during the experiment over virtually 800 hours is shown in FIG. 3.

Figure 3:
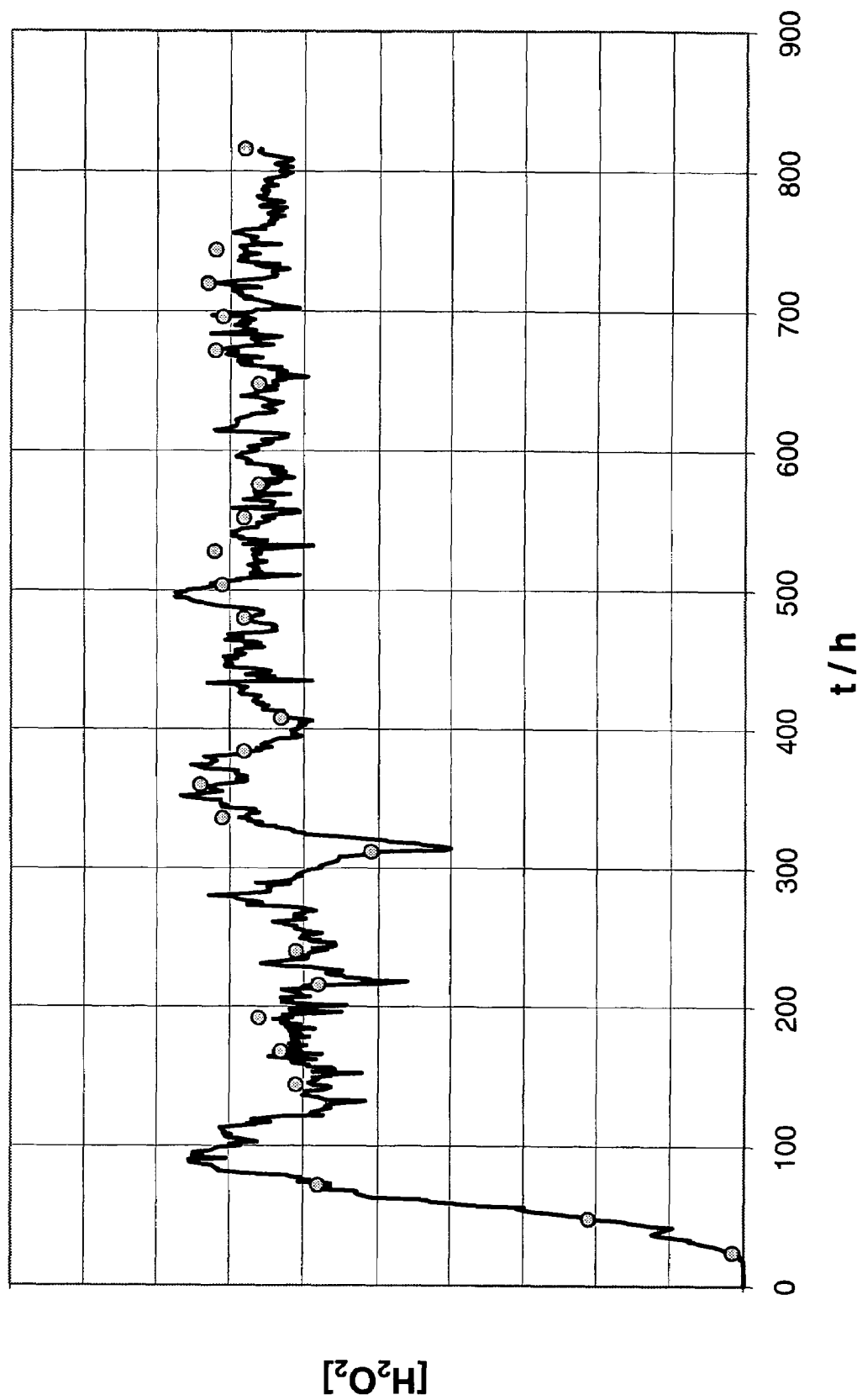

FIG. 3 shows a comparison of the hydrogen peroxide content of the output from the reactor described in the example determined by the on-line and off-line methods. (The on-line method is indicated in FIG. 3 by means of a line, while the off-line method is indicated by circular measurement points.)

The good agreement between the on-line and off-line determinations of the hydrogen peroxide content demonstrates the quality of the measurement. A purely off-line determination would not be sufficient to achieve the desired continuous adjustment of the temperature or to keep the hydrogen peroxide conversion constant.

| Reference numerals for FIG. 1 | |
|---|---|
| 1 = | Line for taking the sample |
| 2 = | Sampling valve |
| 3 = | Measurement cell |
| 4 = | Transmission probe |
| 5 = | Optic fibers |
| 6 = | Trigger signal |
| 7 = | Spectrometer |
| 8 = | Light source |
| 9 = | Signal proportional to the $H_2O_2$ concentration from computer or data processing system to process control system |
| 10 = | Control commands from process control system to the process |
| 11 = | Propylene oxide plant |
| 12 = | Process titrator |
| 13 = | Discharge to waste |
| 14 = | Solvent |
| 15 = | Color reagent |

We claim:
1. A method for continuously oxidizing an alkene, in a synthesis plant comprising a process control system, the method comprising
reacting the alkene with hydrogen peroxide in the presence of a catalyst in the synthesis plant,
determining, selectively, the hydrogen peroxide content of the reaction mixture on-line by an apparatus for the selective on-line determination of hydrogen peroxide, thereby creating reaction hydrogen peroxide content data,
evaluating the data determined by the apparatus by means of at least one data processing unit, and
converting the data into control commands for process control of the synthesis plant, wherein the reaction conditions of the alkene with hydrogen peroxide in the presence of the catalyst are altered by the process control system to keep the residual hydrogen peroxide content of the reaction mixture within predetermined limits, wherein the selective on-line determining of the hydrogen peroxide content of the reaction comprises at least the following steps (1) admixing a sample of the reaction mixture comprising hydrogen peroxide with at least one reagent which forms a substance that can be detected by optical methods upon reaction of the reagent with the hydrogen peroxide, so as to form the substance, and (2) determining the amount of the substance present by measuring its specific absorption in an appropriate wavelength range, wherein the at least one reagent comprises a leuco dye and a peroxidase, or is selected from the group consisting of metals of transition groups IV to IX of the Periodic Table of the elements, or is at least one compound selected from the group consisting of titanium-, cobalt-, chromium-, zirconium-, hafnium-, vanadium-, niobium- and tantalum-containing compounds, wherein the apparatus for the selective on-line determining of the hydrogen peroxide comprises at least one sampling device for taking a sample from the reaction mixture formed in the course of the synthesis, at least one sample preparation apparatus, at least one instrument which is capable of determining the specific absorption of the sample in a suitable wavelength range, and at least one component which is connected to the at least one sampling device, the at least one sample preparation apparatus, and the at least one instrument, and performs a control function for, and coordinates the operation of, the at least one sampling device, the at least one sample preparation apparatus, and the at least one instrument, and wherein the at least one data processing unit for evaluating the data determined by the apparatus for the selective on-line determination of hydrogen peroxide and for converting the data into control commands is connected to the apparatus wherein the control commands are then passed on to the process control system of the synthesis plant, which process control system is connected to the at least one data processing unit.

2. The method of claim 1, wherein the catalyst is a zeolite catalyst.

3. The method of claim 2, wherein the zeolite catalyst is a titanium silicalite having an MFI structure.

4. The method of claim 1,
wherein the alkene is propene,
wherein the propene is reacted with the hydrogen peroxide in a methanolic solution to form propylene oxide, and
wherein the catalyst is a titanium silicalite having an MFI structure.

5. The method of claim 1, wherein the reacting is carried out in a plurality of reactors, and
wherein the hydrogen peroxide content is determined on-line in at least one reactor.

6. The method of claim 5, wherein the hydrogen peroxide content is determined in all of the reactors.

7. The method of claim 1, wherein the at least one reagent is at least one compound selected from the group consisting of titanium-, cobalt-, chromium-, zirconium-, hafflium-, vanadium-, niobium-, and tantalum-containing compounds.

8. The method of claim 1, wherein suitable wave length range is in the UV/VIS region of the spectrum.

9. A method for continuously oxidizing propene, in a synthesis plant comprising a process control system, the method comprising reacting, in a plurality of reactors, the propene with hydrogen peroxide in a methanolic solution in the presence of a titanium-silicalite catalyst having an MFI structure to form propylene oxide in the synthesis plant, determining the hydrogen peroxide content of the reaction in at least one reactor on-line by an apparatus for the on-line determination of hydrogen peroxide, thereby creating reaction hydrogen peroxide content data, evaluating the data determined by the apparatus by means of at least one data processing unit, and converting the data into control commands for process control of the synthesis plant, wherein the reaction of the alkene with hydrogen peroxide in the presence of the catalyst is altered by the process control system to keep the residual hydrogen peroxide content of the reaction in the at least one reactor within predetermined limits, wherein the on-line determining of the hydrogen peroxide content of the reaction comprises admixing a sample of the reaction comprising hydrogen peroxide with at least one reagent which forms a substance that can be detected by optical methods upon reaction of the reagent with the hydrogen peroxide, so as to form the substance, and determining the amount of the substance present by measuring its specific absorption in an appropriate wavelength range, wherein the at least one reagent comprises a leuco dye and a peroxidase, or is selected from the group consisting of metals of transition groups IV to IX of the Periodic Table of the elements, or is at least one compound selected from the group consisting of titanium-, cobalt-, chromium-, zirconium-, hafnium-, vanadium-, niobium- and tantalum-containing compounds, wherein the apparatus for the on-line determining of the hydrogen peroxide comprises at least one sampling device for taking a sample from the reaction mixture formed in the course of the synthesis, at least one sample preparation apparatus, at least one instrument which is capable of determining the specific absorption of the sample in a suitable wavelength range, and at least one component which is connected to the at least one sampling device, the at least one sample preparation apparatus, and the at least one instrument, and performs a control function for, and coordinates the operation of, the at least one sampling device, the at least one sample preparation apparatus, and the at least one instrument, and wherein the at least one data processing unit for evaluating the data determined by the apparatus for the on-line determination of hydrogen peroxide and for converting the data into control commands is connected to the apparatus wherein the control commands are then passed on to the process control system of the synthesis plant, which process control system is connected to the at least one data processing unit.

10. The method of claim 9, wherein the determining is conducted on samples taken from all of the reactors.

11. The method of claim 9, wherein the at least one reagent is at least one compound selected from the group consisting of titanium-, cobalt-, chromium-, zirconium-, hafnium-, vanadium-, niobium-, and tantalum-containing compounds, and wherein the suitable wavelength range is in the UV/VIS region of the spectrum.

12. The method of claim 9, wherein the at least one reagent comprises a leuco dye and a peroxidase and wherein the suitable wavelength range is in the UV/VIS region of the spectrum.

* * * * *